United States Patent [19]

Kino et al.

[11] Patent Number: 5,474,918
[45] Date of Patent: Dec. 12, 1995

[54] PROCESS FOR THE PRODUCTION OF L-THREONINE AND L-ISOLEUCINE BY FERMENTATION OF *ESCHERICHIA COLI*

[75] Inventors: Kuniki Kino; Kazuyuki Okamoto; Yasuya Takeda; Yoshiyuki Kuratsu, all of Houfu, Japan

[73] Assignee: Kyowa Kakko Kogyo Co., Ltd., Tokyo, Japan

[21] Appl. No.: 282,816

[22] Filed: Jul. 29, 1994

Related U.S. Application Data

[63] Continuation of Ser. No. 21,888, Feb. 24, 1993, abandoned.

[30] Foreign Application Priority Data

Feb. 25, 1992 [JP] Japan ................................. 4-038121
Nov. 25, 1992 [JP] Japan ................................. 4-314755

[51] Int. Cl.$^6$ ..................... C12P 13/08; C12P 13/06; C12P 13/04
[52] U.S. Cl. ..................... 435/115; 435/116; 435/106; 435/252.8
[58] Field of Search ..................... 435/106, 116, 435/115, 252.8

[56] References Cited

U.S. PATENT DOCUMENTS

| | | | |
|---|---|---|---|
| 3,622,453 | 11/1993 | Akeyama et al. | 435/115 |
| 5,017,483 | 5/1991 | Furukawa et al. | 435/115 |

FOREIGN PATENT DOCUMENTS

| | | |
|---|---|---|
| 0445830 A2 | 3/0891 | European Pat. Off. . |
| 0213536 | 3/1987 | European Pat. Off. . |
| 51-6752 | 3/1976 | Japan . |
| 53-069881 | 6/1978 | Japan . |
| 56-10037 | 3/1981 | Japan . |
| 56-039792 | 4/1981 | Japan . |
| 63-273487 | 11/1988 | Japan . |
| 63-126998 | 11/1989 | Japan . |
| 2-458 | 1/1990 | Japan . |
| 3-259088 | 11/1991 | Japan . |

OTHER PUBLICATIONS

Livshits, Chem. Ab., 81:87848b (1974).
Kochharyan, et al., Chem. Ab., 85:119479H (1976).
Kocharyan, et al., Chem. Ab., 90:115816w (1979).
Livshits, Chem. Ab., 83:119480b (1976).
Kocharyan, et al., Chem. Ab., 88:59997a (1978).
Levine, et al., Mol. Gen., Genet, 181:3138 (1981).

*Primary Examiner*—Marian C. Knode
*Assistant Examiner*—Maria L. Osoteo
*Attorney, Agent, or Firm*—Limbach & Limbach; W. Patrick Bengtsson

[57] ABSTRACT

A process for the production of L-threonine by fermentation of *Escherichia coli* FERM BP-3756 or *Escherichia coli* FERM BP-4072 and a process for the production of L-isoleucine by the fermentation of *Escherichia coli* FERM BP-3757 is disclosed. The strains are resistant to purine analogues such as 6-dimethylaminopurine or 6-methylaminopurine.

2 Claims, No Drawings

PROCESS FOR THE PRODUCTION OF L-THREONINE AND L-ISOLEUCINE BY FERMENTATION OF *ESCHERICHIA COLI*

This is a continuation of application Ser. No. 08/021,888 filed on Feb. 24, 1993, now abandoned.

All microorganism deposits were made under the Budapest Treaty. *Escherichia coli* H-8311 was deposited on Aug. 21, 1991 as FERM BP-3520. *Escherichia coli* H-8285 was deposited on Oct. 29, 1991 as FERM BP-3629. *Escherichia coli* H-8624 was deposited on Nov. 11, 1992 as FERM BP-4072. *Escherichia coli* H-8460 was deposited on Feb. 21, 1992 as FERM BP-3756. *Escherichia coli* H-8461 was deposited on Feb. 21, 1992 as FERM BP-3757. All microorganisms were deposited with Fermentation Research Institute, Agency of Industrial Science and Technology, Ministry of International Trade and Industry, 1–3 Higashi, 1-chome, Tsukuba-shi, Ibaraki-ken, Japan (Postal Code: 305). All restrictions on the availability to the public of the deposited microorganisms will be irrevocably removed upon the granting of a patent for this application.

BACKGROUND OF THE INVENTION

The present invention relates to a process for the production of L-threonine or L-isoleucine by fermentation. L-threonine and L-isoleucine are useful as a medicament such as an amino acid preparation and can also be used as an animal feed additive.

Several processes for producing L-threonine by fermentation comprising the use of a microorganism belonging to the genus Escherichia are known including a process using a microorganism having a borrelidin sensitivity (Japanese Published Examined Patent Application No. 6752/76), a process using a microorganism requiring diaminopimelic acid and methionine for growth and having a threonine biosynthetic system with resistance to feedback inhibition by threonine (Japanese Published Examined Patent Application No. 10037/81), and a process using microorganisms having a resistance to at least one of rifampicin, lysine, methionine, aspartic acid, and homoserine, or with the decreased ability to decompose L-threonine (Japanese Published Unexamined Patent Application No. 273487/88, U.S. Pat. No. 5017483).

The present applicant has applied for a patent on a process that uses a microorganism having a resistance to L-serine and/or ethionine (Japanese Published Unexamined Patent Application No. 259088/91, European Publication No. 445830) and a process that uses a microorganism having a resistance to L-phenylalanine and/or L-leucine in the presence of L-lysine (Japanese Patent Application No. 224259/91). On the other hand, few reports have been made for a process for the production of L-isoleucine by fermentation comprising the use of a microorganism belonging to the genus Escherichia, or as a process using a mutant. Rather, only a process that uses a microorganism having a resistance to an isoleucine analogue and further having a resistance to arginine hydroxamate and/or ethionine has been applied for a patent by the present applicant (Japanese Patent Application No. 294420/91).

In addition, there is also known a process that uses a microorganism belonging to the genus Escherichia having the activity of threonine deaminase or acetohydroxy acid synthase (i.e., key enzymes of synthesizing L-isoleucine) increased by recombinant DNA technology (Japanese Published Unexamined Patent Application No. 458/90). This prior art process, however, is not insufficient since the yield of isoleucine formed is low.

SUMMARY OF THE INVENTION

The present invention relates to a process for producing either L-threonine or L-isoleucine by fermentation, by culturing in a medium a microorganism belonging to the species *Escherichia coli* where that microorganism has both the ability to produce either L-threonine or L-isoleucine and a resistance to a purine analogue such as 6-dimethylaminopurine or 6-methylaminopurine.

DETAILED DESCRIPTION OF THE INVENTION

Any microorganism may be used in the present invention so long as it belongs to the genus Escherichia and has a resistance to a purine analogue and the ability to produce L-threonine or L-isoleucine.

The purine analogue resistance of the microorganism used in the present invention refers to resistance to 6-dimethylaminopurine, 6-methylaminopurine, 6-mercaptopurine, 8-azaadenine, 8-azadiaminopurine, etc.

According to a conventional mutagenesis, the L-threonine- or L-isoleucine-producing microorganism of the present invention can be obtained by imparting the purine analogue-resistance to an microorganism belonging to the genus Escherichia capable of producing of L-threonine or L-isoleucine. Alternatively, the mutant strain can also be obtained by endowing a purine analogue-resistant mutant strain derived from a wild-type strain with a mutation for the improvement of L-threonine or L-isoleucine productivity, such as nutrient requirement or threonine (or isoleucine) metabolic antagonist resistance. Preferred examples of the suitable microorganism include *Escherichia coli* H-8460, H-8461, and H-8624.

Production of L-threonine or L-isoleucine using the microorganism of the present invention can be effected by culturing the microorganism in a conventional manner.

Any synthetic or natural medium may be used in the present invention as long as it appropriately contains carbon sources, nitrogen sources, inorganic compounds, and trace amounts of other nutrients required for the strain used.

Carbon sources that may be employed in the present invention include carbohydrates such as glucose, fructose, lactose, molasses, cellulose hydrolyzates, crude sugar hydrolyzates, starch hydrolyzates, etc.; and organic acids such as pyruvic acid, acetic acid, fumaric acid, malic acid, lactic acid. etc. Depending upon the assimilability of a microorganism used, alcohols such as glycerol, ethanol, etc., can also be employed.

Nitrogen sources that may be employed in the present invention include ammonia and various inorganic and organic ammonium salts, such as ammonium chloride, ammonium sulfate, ammonium acetate, ammonium phosphate, etc., amines and other nitrogen-containing compounds, as well as peptone, meat extract, corn steep liquor, casein hydrolyzates, soybean cake hydrolyzates, various fermented bacterial cells or their digested product, etc.

Inorganic compounds that may be employed in the present invention include potassium dihydrogen phosphate, dipotassium hydrogen phosphate, magnesium phosphate, magnesium sulfate, sodium chloride, ferrous sulfate, manganese sulfate, copper sulfate, calcium carbonate. etc.

Culturing is carried out under aerobic conditions, for example, by submerged shaking culture or aeration-agitation culture. The temperature for the culturing is in the range of 20°–40° C., preferably 25°–38° C. The pH of the medium is in the range of pH 5–9, preferably maintained around neutrality. During the culturing, the pH of the medium is adjusted by using calcium carbonate, inorganic and organic acids, alkali solution, ammonia, pH buffer, etc. Usually, after culturing for 2–7 days, L-threonine or L-isoleucine is accumulated in the culture.

After the completion of culturing, precipitates such as bacterial cells etc. are removed from the culture by means of centrifugation, etc., and L-threonine or L-isoleucine can be recovered from the supernatant by a combination of techniques such as a treatment with ion-exchange, concentration, salting-out, etc.

Hereinafter the present invention is specifically described with reference to the examples.

EXAMPLE 1

Acquirement of mutant strain (1)

L-threonine-producing *Escherichia coil* H-8311 (FERM BP-3520) was subjected to a conventional mutation treatment with N-methyl-N'-nitro-N-nitrosoguanidine (0.2 mg/ml) at 30° C. for 30 minutes. Subsequently, the cells were spread on a minimum medium containing 1.5 g/l 6-dimethylaminopurine (0.5% glucose, 0.2% $NH_4Cl$, 0.2% $KH_2PO_4$, 0.01% $MgSO_4.7H_2O$, 20 mg/l $FeSO_4.7H_2O$, 50 mg/l DL-methionine, and 2% agar, pH 7.2). After culturing at 30° C. for 2–6 days, large colonies grown on the medium were picked up and separated as 6-dimethylaminopurine-resistant mutant, whereby H-8460 was obtained. This bacterial strain was deposited with Fermentation Research Institute, Agency of Industrial Science and Technology, Japan, on Feb. 21, 1992, under the Budapest treaty, with the accession No. FERM BP-3756.

Separately, an L-isoleucine-producing microorganism, *Escherichia coli* H-8285 (FERM BP-3629: Japanese Patent Application 294420/91), was subjected to mutation treatment in the same manner as described above. Then, the cells were spread on a 1.5 g/l 6-dimethylaminopurine-containing minimum medium with the same composition as described above. After culturing at 30° C. for 2–6 days, large colonies grown on the medium were picked up and separated as 6-dimethylaminopurine-resistant mutant, whereby H-8461 was obtained. This bacterial strain was deposited with Fermentation Research Institute, Agency of Industrial Science and Technology, Japan, on Feb. 21, 1992, under the Budapest treaty, with the accession No. FERM BP-3757. Because of the diaminopimelic acid requirement of its parent strain H-8285, 200 mg/l diaminopimelic acid was added to the above minimum medium for the acquirement of H-8461.

The thus obtained mutants were compared with their respective parent strains with respect to the degrees of resistance to 6-dimethylaminopurine. The degree of resistance was expressed in terms of degree of growth. That is, each strain was cultured in a complete medium (1% trypton, 0.5% yeast extract, 1% NaCl, and 200 mg/l diaminopimelic acid, pH 7.5) for 24 hours in a slant. The cells were then suspended in a sterilized water and the obtained suspensions each were spread on a minimum medium (0.5% glucose, 0.2% $NH_4Cl$, 0.2% $KH_2PO_4$, 0.01% $MgSO_4.7H_2O$, 20 mg/l $FeSO_4.7H_2O$, 50 mg/l DL-methionine, 200 mg/l diaminopimelic acid, and 2% agar, pH 7.5) containing 6-dimethylaminopurine in the amounts set forth in Table 1 and culturing was carried out at 30° C. for 72 hours. The results are shown in Table 1.

TABLE 1

| Strain | 6-dimethylaminopurine (g/l) | | |
|---|---|---|---|
|  | 0 | 1.0 | 1.5 |
| H-8311 | + | ± | – |
| H-8460 | + | + | + |
| H-8285 | + | ± | – |
| H-8461 | + | + | + |

+: sufficient growth ±: slight growth –: no growth

Acquirement of mutant strain (2)

L-threonine-producing *Escherichia coli* H-8311 (FERM BP-3520) was subjected to a conventional mutation treatment with N-methyl-N'-nitro-N-nitrosoguanidine (0.2 mg/ml) at 30° C. for 30 minutes. Subsequently, the cells were spread on a minimum medium containing 1.0 g/l 6-methylaminopurine (0.5% glucose, 0.2% $NH_4Cl$, 0.2% $KH_2PO_4$, 0.01% $MgSO_4.7H_2O$, 20 mg/l $FeSO_4.7H_2O$, 50 mg/l DL-methionine, and 2% agar, pH 7.2). After culturing at 30° C. for 2–6 days, large colonies grown on the medium were picked up and separated as 6-methylaminopurine-resistant mutant, whereby H-8624 was obtained. This bacterial strain was deposited with Fermentation Research Institute, Agency of Industrial Science and Technology, Japan, on Nov. 11, 1992. under the Budapest treaty, with the accession No. FERM BP-4072.

The thus obtained mutant was compared with the parent strain with respect to the degrees of resistance to 6-methylaminopurine. The degree of resistance was expressed in terms of degree of growth. That is, each strain was cultured in a complete medium (1% trypton. 0.5% yeast extract, 1% NaCl, and 200 mg/l diaminopimelic acid, pH 7.5) for 24 hours in a slant. The cells were then suspended in a sterilized water and the obtained suspensions each were spread on a minimum medium (0.5% glucose, 0.2% $NH_4Cl$, 0.2% $KH_2PO_4$, 0.01% $MgSO_4.7H_2O$, 20 mg/l $FeSO_4.7H_2O$, 50 mg/l DL-methionine, 200 mg/l diaminopimelic acid, and 2% agar, pH 7.5) containing 6-methylaminopurine in the amounts set forth in Table 2 and culturing was carried out at 30 ° C. for 72 hours. The results are shown in Table 2.

TABLE 2

| Strain | 6-dimethylaminopurine (g/l) | | |
|---|---|---|---|
|  | 0 | 0.5 | 1.0 |
| H-8311 | + | + | – |
| H-8624 | + | + | + |

+: sufficient growth –: no growth

EXAMPLE 2

L-threonine Production Test

The mutants obtained in Example 1 were examined for fermentation production of L-threonine.

*Escherichia coli* H-8311, *Escherichia coli* H-8460, and *Escherichia coli* H-8624, respectively, were cultured with shaking at 30° C. for 16 hours in a seed medium (pH 7.4) containing 2% glucose, 1% peptone, 1% yeast extract, and 0.25% NaCl. Then, 100 ml of the resulting seed culture was inoculated into 2 1-jar fermentor containing 1 l of the fermentation medium as set forth below, followed by culturing with stirring at 800 rpm at 30° C. and an aeration rate of 1 liter/min. During the culturing, aqueous ammonia was added to the culture to adjust the pH to 6.5±0.2 and supply a nitrogen source. Glucose and $KH_2PO_4$ were also supplied at an appropriate time. The culture was carried out for 70 hours. After the completion of the culturing, the amount of L-threonine accumulated was quantitatively analyzed by high performance liquid chromatography. The results are shown in Table 3.

TABLE 3

| Strain | L-threonine (g/l) |
|---|---|
| H-8311 | 65.3 |
| H-8460 | 76.5 |
| H-8624 | 74.8 |

Fermentation medium composition: 4% glucose, 1.2% $(NH_4)_2SO_4$, 0.2% $KH_2PO_4$, 0.01% $MgSO_4.7H_2O$, 0.5% corn steep liquor, and 0.3 g/l DL-methionine, at pH 7.4.

One liter of the L-threonine-containing fermentation broth obtained by culturing H-8460 strain described above was centrifuged at 3,000 rpm for 10 minutes, whereby the bacterial cells and other impurities were removed. The thus obtained supernatant was passed through a column packed with strongly acidic cationic ion exchange resin Diaion SK1B ($H^+$ type; product of Mitsubishi Kasei Corporation, Japan), so that L-threonine was adsorbed thereto. After the column was washed with water, the sample was eluted with 0.5N aqueous ammonia to collect L-threonine fractions. The collected fractions were concentrated and ethanol was added to the concentrate. By storing the mixture under cooling, 61.4 g of L-threonine crystals (purity: 98% or more) were obtained.

EXAMPLE 3

L-isoleucine Production Test

The mutants obtained in Example 1 were examined for fermentation production of L-isoleucine.

*Escherichia coil* H-8285 and *Escherichia coil* H-8461 were cultured respectively with shaking at 30° C. for 16 hours in a seed medium (pH 7.4) prepared by adding 0.02% diaminopimelic acid to the seed medium used in Example 2. Then, 100 ml of the resulting seed culture was inoculated into 2 l-jar fermentor containing 1 l of the fermentation medium as set forth below, followed by culturing with stirring at 800 rpm at 30° C. and an aeration rate of 1 liter/min. During the culturing, aqueous ammonia was added to the culture to adjust the pH to 6.5±0.2 and supply a nitrogen source. Glucose was supplied at an appropriate time. The culture was carried out for 45 hours. After the completion of the culturing, the amount of L-isoleucine accumulated was quantitatively analyzed by high performance liquid chromatography. The results are shown in Table 4.

TABLE 4

| Strain | L-isoleucine (g/l) |
|---|---|
| H-8285 | 26.7 |
| H-8461 | 30.2 |

Fermentation medium composition: 4% glucose, 0.5% $(NH_4)_2SO_4$, 0.1% $KH_2PO_4$, 0.01% $MgSO_4.7H_2O$, 0.5% corn steep liquor, 0.35 g/l DL-methionine, and 0.9 g/l diaminopimelic acid, at pH 7.4.

One liter of the L-isoleucine-containing fermentation broth obtained by culturing H-8461 strain described above was centrifuged at 3,000 rpm for 10 minutes, whereby the bacterial cells and other impurities were removed. The thus obtained supernatant was passed through a column packed with strongly acidic cationic ion exchange resin Diaion SK1B ($H^+$ type; product of Mitsubishi Kasei Corporation, Japan), so that L-isoleucine was adsorbed thereto. After the column was washed with water, the sample was eluted with 0.5N aqueous ammonia to collect L-isoleucine fractions. The collected fractions were concentrated and ethanol was added to the concentrate. By storing the mixture under cooling, 22.0 g of L-isoleucine crystals (purity: 98% or more) were obtained.

What is claimed is:

1. A process for the production of L-threonine by fermentation which comprises:

culturing in a nutrient medium a microorganism which is selected from the group consisting of *Escherichia coli* FERM BP-3756 and *Escherichia coli* FERM BP-4072 under conditions sufficient for the production of L-threonine, and recovering L-threonine therefrom.

2. A process for the production of L-isoleucine by fermentation, which comprises:

culturing in a nutrient medium *Escherichia coli* FERM BP-3757 under conditions sufficient for the production of L-isoleucine, and recovering L-isoleucine therefrom.

* * * * *